(12) United States Patent
Kroll

(10) Patent No.: US 6,687,542 B2
(45) Date of Patent: Feb. 3, 2004

(54) XY SELECTABLE LEAD ASSEMBLY

(75) Inventor: Mark W. Kroll, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 127 days.

(21) Appl. No.: 09/970,837

(22) Filed: Oct. 3, 2001

(65) Prior Publication Data

US 2003/0069624 A1 Apr. 10, 2003

(51) Int. Cl.[7] .............................................. A61N 1/362
(52) U.S. Cl. ...................................................... 607/9
(58) Field of Search ........................... 607/5, 9, 37, 38, 607/15, 119

(56) References Cited

U.S. PATENT DOCUMENTS

| | | | |
|---|---|---|---|
| 4,991,583 A | 2/1991 | Silvian | 128/419 PG |
| 5,470,348 A | 11/1995 | Neubauer et al. | 607/68 |
| 5,895,416 A | 4/1999 | Barreras, Sr. et al. | 607/62 |
| 6,085,118 A | 7/2000 | Hirschberg et al. | 607/9 |

*Primary Examiner*—Scott M. Getzow

(57) ABSTRACT

An implantable cardiac stimulation lead system for use with a stimulation device includes an implantable housing containing a pulse generator which emits stimulation pulses. The lead system includes a first electrode for delivering stimulation pulse current to tissue, a plurality of second electrodes for returning to the stimulation device the pulse current after traversing the tissue, and a matrix switching system. X and Y electrical conductors extend between the stimulating device and the matrix switching system. The matrix switching system includes a switching device to connect each of the Y electrical conductors to each single X electrical conductor and to each of the second electrodes such that each switching device is actuated by a corresponding pulse from the pulse generator applied to corresponding X and Y conductors connected thereto and such that the total number of electrical conductors required is fewer than the number of the second electrode.

11 Claims, 3 Drawing Sheets

XY SELECTABLE LEAD ASSEMBLY

FIELD OF THE INVENTION

The present invention relates generally to an implantable cardiac stimulation lead and, more particularly, to a technique for dramatically increasing the number of stimulating sites available without a concurrent increase in the number of conductors in the lead.

BACKGROUND OF THE INVENTION

The implantable cardiac stimulation leads with which the present invention is concerned may take the form of pacemakers capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator, commonly known as a "pacemaker" or "pacer", uses one or two flexible leads having one end connected to the pacer and the other end connected to electrodes placed in close proximity to the heart. These leads are used to stimulate or pace the heart. Also, these leads are used to sense the heart activity by picking up electrical signals from the heart.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer case or housing. The case, in turn, makes contact with the body tissue and/or fluids.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated 10 to 20 mm from the tip electrode. The tip electrode is typically placed in contact with heart tissue, while the ring electrode is in electrical contact with the blood. Because both body tissue and fluids are conductive, the ring electrode of a bipolar lead, in contact with the body fluids, serves as an electrical return for both pacing and sensing.

As indicated, pacing or sensing using the pacer case or enclosure as part of the electrical return path is known as unipolar pacing or sensing. Pacing or sensing using the lead ring electrode and associated lead conductor as the electrical return path is known as bipolar pacing or sensing.

There are numerous factors to consider when deciding whether unipolar or bipolar pacing and/or sensing should be used. Bipolar pacing has, in general, the advantage of requiring less energy than unipolar pacing. Further, bipolar sensing is less prone to crosstalk and myopotential sensing than is unipolar sensing. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is preferred if pectoral or diaphragmatic stimulation occurs.

Unipolar pacing and sensing offers the advantage, in general, of simpler circuitry within the pacemaker and a smaller diameter lead. Some physicians prefer unipolar over bipolar pacing and/or sensing as a function of other implantation and heart conditions. Depending on the lead orientation, unipolar sensing may be better than bipolar sensing.

An item of prior art which is pertinent to the present invention is U.S. Pat. No. 4,991,583 to Silvian which discloses a method of operation and an apparatus provided for independently configuring one or both channels of a conventional pacer to either a unipolar or bipolar pacing mode of operation and either a unipolar tip-to-case, unipolar ring-to-case, or a bipolar tip-to-ring sensing mode of operation, despite positive potentials that appear at the tip or ring electrodes.

Another disclosure of interest is provided by U.S. Pat. No. 5,895,416 to Barreras, Sr. et al. which discloses a lead system which steers the electrical field to the appropriate location by switching transistors off and on.

Still another pertinent disclosure is provided by U.S. Pat. No. 6,085,118 to Hirschberg et al. which discloses a lead system which determines the function of an electrode by use of a switching system.

It was in light of the foregoing that the present invention was conceived and has now been reduced to practice.

SUMMARY OF THE INVENTION

The present invention discloses an implantable cardiac stimulation lead system for use with a stimulation device which includes an implantable housing containing a pulse generator which emits stimulation pulses. The lead system includes a first electrode for delivering stimulation pulse current to tissue, a plurality of second electrodes for returning to the stimulation device the pulse current after traversing the tissue, and a matrix switching system. X and Y electrical conductors extend between the stimulating device and the matrix switching system. The matrix switching system includes a switching device to connect each of the Y electrical conductors to each single X electrical conductor and to each of the second electrodes such that each switching device is actuated by a corresponding pulse from the pulse generator applied to corresponding X and Y conductors connected thereto and such that the total number of electrical conductors required is fewer than the number of the second electrodes.

A primary feature, then, of the present invention is the provision of an improved implantable cardiac stimulation lead.

Another feature of the present invention is the provision of such a technique which dramatically increases the number of stimulating sites available without a concurrent increase in the number of conductors in the lead.

Yet another feature of the present invention is the provision of such a technique according to which an implantable cardiac stimulation lead can be provided with multiple stimulation sites with minimal enlargement of lead size.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
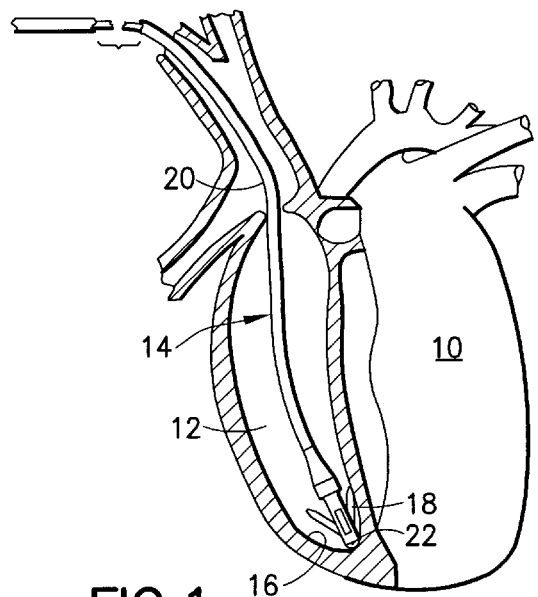
FIG. 1 is a perspective view illustrating a heart with a portion cut away to reveal an implantable lead assembly, embodying the present invention, secured therein to a wall of the heart.

Referring to FIG. 1, there is shown a diagrammatic perspective view partially cut away and shown in section of a heart 10 into the right ventricle 12 of which is inserted a body implantable lead 14 of the endocardial type incorporating features of the present invention. Although the present invention will be described with reference to the embodiments shown in the drawings, it should be understood that the invention can be embodied in many alternate forms or embodiments. In addition, any suitable size, shape or type of elements or materials could be used. The lead 14 is attached to an interior wall 16 of the heart 10 by means of fixing tines 18 which engage the tissue or trabeculae of the heart. However, it is within the purview of the present invention that the lead 14 be of an active fixation construction.

Figure 2:
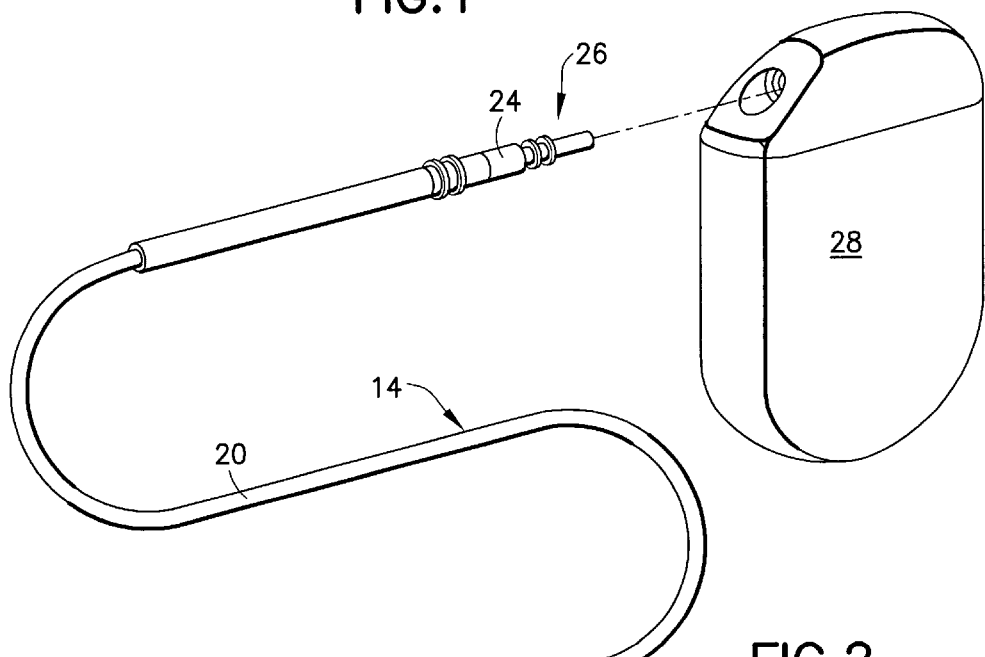
FIG. 2 is a perspective view of an implantable lead embodying the invention in combination with a stimulating device such as a pacemaker.

As further illustrated, the lead 14 also includes an insulating sheath 20 interconnecting a distal electrode 22 secured adjacent the interior wall 16 and an electrical connector 24 at a proximal end 26 to which can be attached a source of electrical energy such as a pacemaker 28 (FIG. 2). Although a pacemaker is mentioned, any desired source of stimulating electrical energy such as a defibrillator could benefit from the invention.

Figure 3:
FIG. 3 is a detail perspective view of an implantable lead illustrating one embodiment of the invention.
Figure 4:
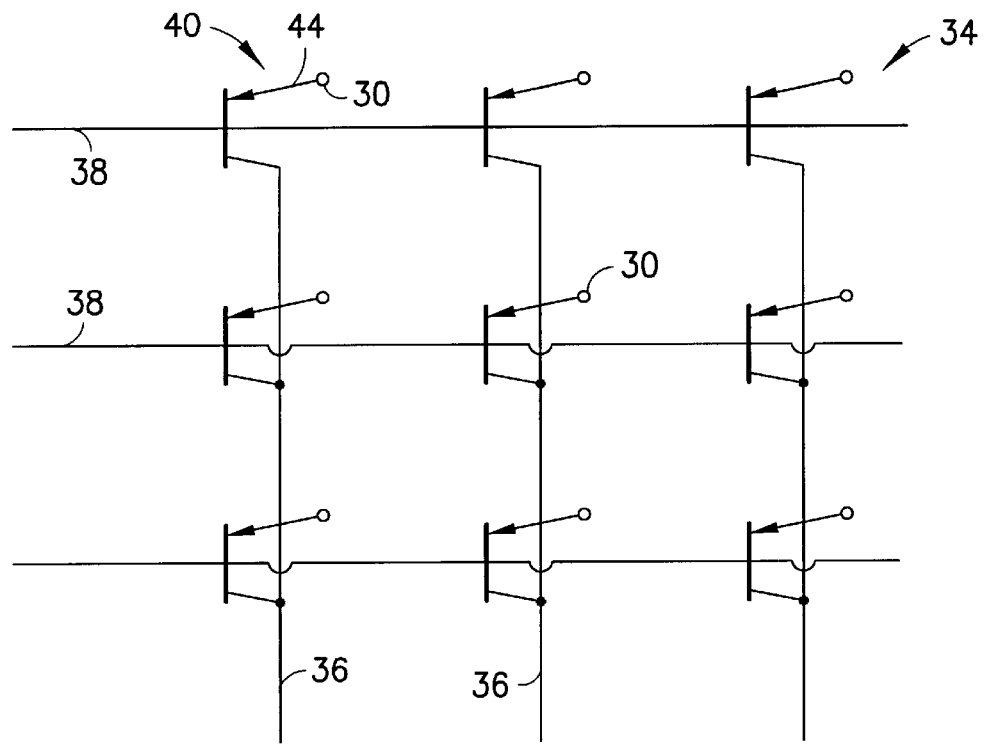
FIG. 4 is a schematic electrical circuit intended for use with the FIG. 3 embodiment.

FIGS. 3 and 4 present the basic concept of the invention with the aid of FIG. 2 already discussed. In this regard, a first electrode in the form of the housing for the pacemaker 28 is provided for delivering a stimulation pulse to tissue, for example, but not necessarily limited to, heart tissue. A plurality of second pacing ring electrodes 30 on a lead 32 (FIG. 3) embodying the present invention are provided for returning to the stimulation device, pacemaker 28, the stimulation current after traversing the heart tissue. In FIG. 4 is illustrated a matrix switching system 34. X electrical conductors 36 extend between the proximal connector 24 (FIG. 2) for releasable coupling to the stimulating device or pacemaker 28 and extend to the matrix switching system 34 for connection to the matrix switching system. In a similar fashion, Y electrical conductors 38 extend between the proximal connector 24 for releasable coupling to the stimulating device and extend also to the matrix switching system 34 for connection thereto.

The matrix switching system 34 is provided with a switching device 40 to connect each of the Y electrical conductors 38 to each single X electrical conductor 36 and also to each of the second electrodes 30. In the event the switching device is a transistor as illustrated, each of the Y electrical conductors 38 controls several associated second electrodes 30 (shown as a ring 30 in FIG. 3.) via an associated emitter 44. A negative voltage on an X line 36 in combination with a negative voltage on a Y line 38 will turn on the transistor 40 to allow current flow through the selected electrode. The X line selects the column while the Y line selects the row in the matrix. While the lead itself does not have this 2-dimensional structure, the electrodes are all forced in line in the mechanical structure. It will be appreciated that while the switching device 40 is illustrated as a transistor, it may take many other forms, for example, a MOSFET (Metal Oxide Semiconductor Field Effect Transistor).

In any event, in accordance with the invention, each of the switching devices 40 is actuated by a corresponding pulse from the pulse generator, that is, pacemaker 28 applied to the corresponding X and Y conductors, 36 and 38, respectively, such that the total number of the X and Y electrical conductors required is fewer than the number of the plurality of the second electrodes.

This resulting benefit can be seen with reference to Table 1 which follows but will be further explained in the description following Table 1.

TABLE 1

| X | Y | Total Conductors | Total Rings | Conductor Savings | Percentage Savings |
|---|---|---|---|---|---|
| 2 | 2 | 4 | 4 | 0 | 0% |
| 3 | 2 | 5 | 6 | 1 | 17% |
| 3 | 3 | 6 | 9 | 3 | 33% |
| 4 | 2 | 6 | 8 | 2 | 25% |
| 4 | 3 | 7 | 12 | 5 | 42% |
| 4 | 4 | 8 | 16 | 8 | 50% |
| 5 | 2 | 7 | 10 | 3 | 30% |
| 5 | 3 | 8 | 15 | 7 | 47% |
| 5 | 4 | 9 | 20 | 11 | 55% |
| 5 | 5 | 10 | 25 | 15 | 60% |
| 6 | 2 | 8 | 12 | 4 | 33% |
| 6 | 3 | 9 | 18 | 9 | 50% |
| 6 | 4 | 10 | 24 | 14 | 58% |
| 6 | 5 | 11 | 30 | 19 | 63% |
| 6 | 6 | 12 | 36 | 24 | 67% |
| 7 | 2 | 9 | 14 | 5 | 36% |
| 7 | 3 | 10 | 21 | 11 | 52% |
| 7 | 4 | 11 | 28 | 17 | 61% |
| 7 | 5 | 12 | 35 | 23 | 66% |
| 7 | 6 | 13 | 42 | 29 | 69% |
| 7 | 7 | 14 | 49 | 35 | 71% |

As already explained, in the array presented as the matrix switching system 34, there is a set of wires 38 that are the Y selector wires and a set of wires 36 that are the X selector wires. Thus, at each pacing ring electrode 30, there is a PNP transistor 40 and in order to turn on that transistor, the Y selector and the X selector must both go to a desired negative pacing voltage. When both of those conditions are present at one site, then there will be a negative voltage at that ring electrode for the pacing operation.

Figure 5:
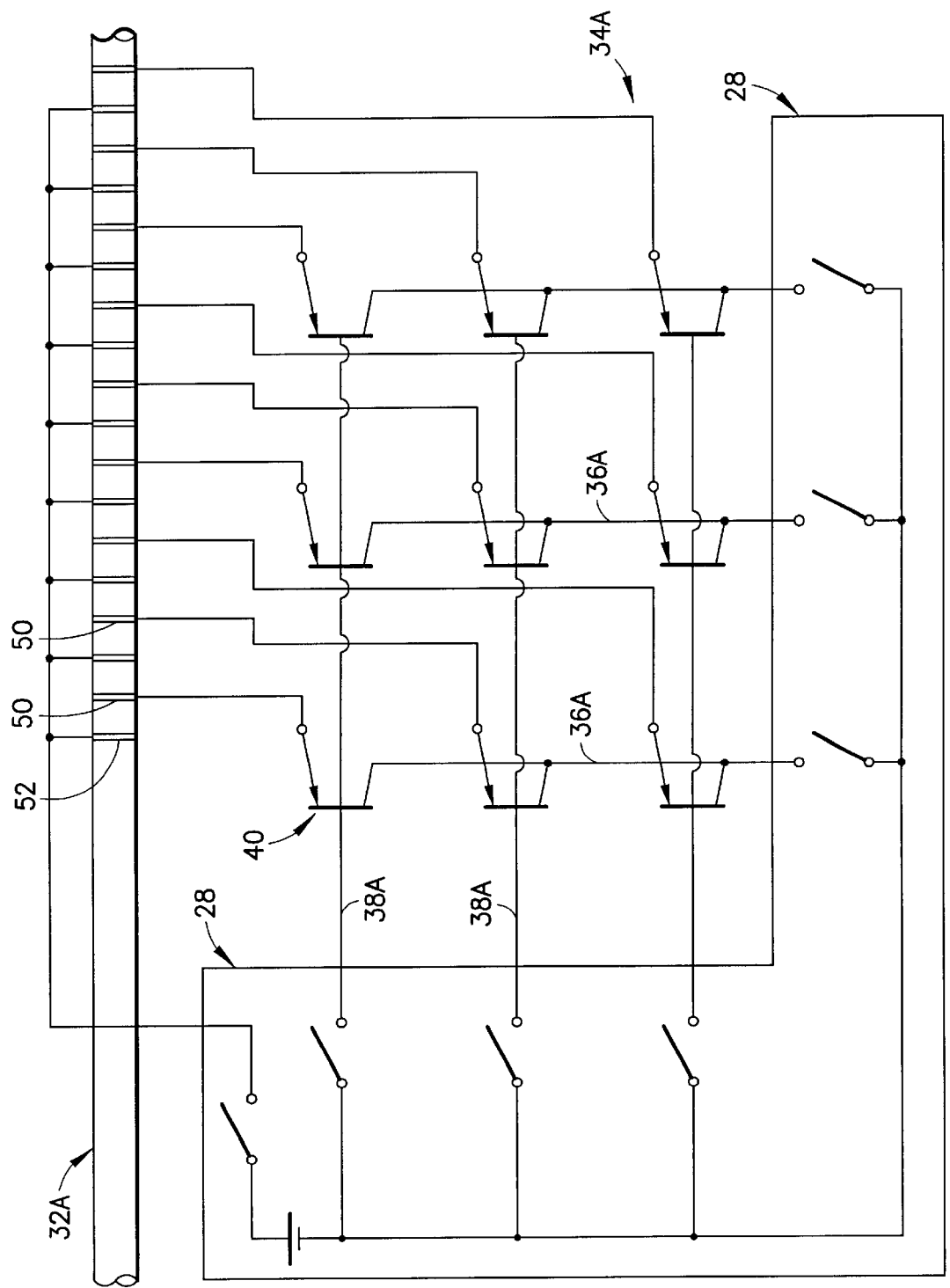
FIG. 5 is a combined diagrammatic representation and schematic electrical circuit of another embodiment of the invention.

As a different embodiment of the invention, FIG. 5 shows a set of "common" ring electrodes 52 on a modified lead 32A connected to be interspersed between active ring electrodes 50 similar to those ring electrodes 30 from the lead 32 of FIG. 3. This allows for a "pseudo" bipolar pacing technique. The ring electrodes 30 in FIG. 3 and the ring electrodes 50 would be pulsed in a unipolar mode, but the ring electrodes 52 in FIG. 5 would be in a common connection to the power supply voltage. Therefore, a local current would be generated. As in the FIG. 4 embodiment, X electrical conductors 36A extend between the proximal connector 24 (FIG. 2) for releasable coupling to the stimulating device or pacemaker 28 and extend to the matrix switching system 34A for connection to the matrix switching system. In a similar fashion, Y electrical conductors 38A extend between the proximal connector for releasable coupling to the stimulating device and extend also to the matrix switching system 34A for connection thereto.

Table 1 shows a significant reduction in wires that are required for pacing. In one instance, for example, there are six X selectors and five Y selectors. There are only 11 wires which can pace 30 ring electrodes and this results in a "savings" of 19 ring electrodes over wires.

If the pacing rings are going to be subjected to defibrillation voltage fields, then they will require some level of protection. One simple type of protection is to use higher voltage transistors. Many other designs, including diode steering networks and current limiters could be employed without detracting from the cost or flexibility.

It should be appreciated that the selectors need not be placed right at the ring. It is not as difficult to run a number of wires through a catheter as it is to run them through a can because of the cost of the header and feedthroughs. Therefore, all selection circuitry could be contained in a hermetically sealed hybrid located at the proximal end of the catheter.

In keeping with the spirit of this invention the distal tip of the lead would be connected through the switching matrix just as the rings are. As an alternative embodiment, the distal tip would have a dedicated conductor for itself. This dedicated line would allow the continuous sensing of the cardiac activity regardless of the matrix selection status.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable cardiac stimulation lead system for use with a stimulation device including an implantable housing containing a pulse generator which emits stimulation pulses, the lead system comprising:
a plurality of electrodes that return to the stimulation device stimulation pulse current after traversing heart tissue; and
a matrix switching system comprising:
X electrical conductors extending between a proximal connector releasably coupled to the stimulation device and extending to the matrix switching system and connected thereto;
Y electrical conductors extending between the proximal connector releasably coupled to the stimulation device and extending to the matrix switching system and connected thereto; and
wherein the matrix switching system comprises a switching array comprising plural switching devices to connect within the switching array each of the Y electrical conductors to each single X electrical conductor and also to each of the electrodes;
wherein one of the switching devices is actuated by a corresponding pulse from the pulse generator applied to corresponding X and Y conductors connected to the switching device.

2. The lead system of claim 1, wherein the electrodes are mutually spaced ring electrodes distant from the housing.

3. The lead system of claim 1, wherein each switching device is a PNP transistor.

4. The lead system of claim 1, wherein the stimulation device is a pacemaker.

5. The lead system of claim 1, wherein the stimulation device is a defibrillator.

6. An implantable cardiac stimulation lead system for use with a stimulation device including an implantable housing containing a pulse generator which emits stimulation pulses, the lead system comprising:
a plurality of first electrodes formed on or in the lead body for delivering a stimulation pulse current to tissue;
a plurality of second electrodes for returning to the stimulation device the stimulation pulse current after traversing the tissue;
a matrix switching system;
X electrical conductors extending between a proximal connector releasably coupled to the stimulating device and extending to the matrix switching system and connected thereto; and
Y electrical conductors extending between the (or a) proximal connector releasably coupled to the stimulating device and extending to the matrix switching system and connected thereto;
wherein the matrix switching system has a switching device to connect within the matrix switching system each of the Y electrical conductors to each single X electrical conductor and also to each of the second electrodes;
wherein each of the switching devices is actuated by a corresponding pulse from the pulse generator applied to corresponding X and Y conductors connected thereto such that the total number of X and Y electrical conductors required is fewer than the number of the plurality of the second electrodes.

7. The lead system of claim 6:
wherein the first electrode is the implantable housing; and
wherein the second electrodes are mutually spaced ring electrodes distant from the housing.

8. The lead system of claim 6, wherein each switching device is a PNP transistor.

9. The lead system of claim 6, wherein the stimulation device is a pacemaker.

10. The lead system of claim 6, wherein the stimulation device is a defibrillator.

11. The lead system of claim 6 in which at least some of the Y conductors connect to each and every X conductor.

* * * * *